United States Patent
Chen et al.

(10) Patent No.: US 11,117,876 B2
(45) Date of Patent: Sep. 14, 2021

(54) CRYSTALLINE FORM OF OZANIMOD HYDROCHLORIDE, AND PROCESSES FOR PREPARATION THEREOF

(71) Applicant: RECEPTOS, LLC, New York, NY (US)

(72) Inventors: Minhua Chen, Suzhou (CN); Yanfeng Zhang, Suzhou (CN); Xiaoting Zhai, Suzhou (CN); Kaiqiang Yan, Suzhou (CN); Chaohui Yang, Suzhou (CN)

(73) Assignee: RECEPTOS LLC, New York, NY (US)

( * ) Notice: Subject to any disclaimer, the term of this patent is extended or adjusted under 35 U.S.C. 154(b) by 0 days.

(21) Appl. No.: 16/643,011

(22) PCT Filed: Aug. 23, 2018

(86) PCT No.: PCT/CN2018/102034
§ 371 (c)(1),
(2) Date: Feb. 28, 2020

(87) PCT Pub. No.: WO2019/042219
PCT Pub. Date: Mar. 7, 2019

(65) Prior Publication Data
US 2020/0339524 A1    Oct. 29, 2020

(30) Foreign Application Priority Data

Aug. 31, 2017   (CN) .......................... 201710768645.3

(51) Int. Cl.
*C07D 271/06*       (2006.01)
(52) U.S. Cl.
CPC ........ *C07D 271/06* (2013.01); *C07B 2200/13* (2013.01)
(58) Field of Classification Search
CPC .................................................. C07D 271/06
See application file for complete search history.

(56) References Cited

U.S. PATENT DOCUMENTS

| | | |
|---|---|---|
| 2011/0172202 A1 | 7/2011 | Martinborough et al. |
| 2019/0241530 A1 | 8/2019 | Sheng et al. |
| 2019/0248755 A1 | 8/2019 | Chen et al. |
| 2019/0337908 A1 | 11/2019 | Chen et al. |
| 2020/0031784 A1 | 1/2020 | Sheng et al. |
| 2020/0157065 A1 | 5/2020 | Chen et al. |
| 2020/0216404 A1 | 7/2020 | Chen et al. |

FOREIGN PATENT DOCUMENTS

| | | |
|---|---|---|
| CN | 102118972 A | 7/2011 |
| CN | 102762100 A | 10/2012 |
| CN | 107840830 A | 3/2018 |
| WO | 2009/151529 A1 | 12/2009 |
| WO | 2011/060392 A1 | 5/2011 |
| WO | WO-2015/066515 A1 | 5/2015 |
| WO | 2016/164180 A1 | 10/2016 |
| WO | WO-2017/215617 A1 | 12/2017 |
| WO | 2018/049632 A1 | 3/2018 |
| WO | WO-2018/050091 A1 | 3/2018 |

OTHER PUBLICATIONS

International Search Report and Written Opinion for Application No. PCT/CN2018/102034, dated Nov. 29, 2018, 11 pages.
Campeta et al., Development of a targeted polymorph screening approach for a complex polymorphic and highly solvating API. J Pharm Sci. Sep. 2010;99(9):3874-86.
U.S. Appl. No. 16/310,328, filed Dec. 14, 2018, 2019-0337908.
U.S. Appl. No. 16/748,303, filed Jan. 21, 2020, 2020-0157065.
U.S. Appl. No. 16/326,353, filed Feb. 18, 2019.
U.S. Appl. No. 16/333,075, filed Mar. 13, 2019, 2019-0248755.
Byrn et al., Pharmaceutical solids: a strategic approach to regulatory considerations. Pharm Res. 1995;12(7):945-954.
Caira, Crystalline Polymorphism of Organic Compounds. Topics in Current Chemistry. 1998;198;163-208.
Huan, Journal of International Pharmaceutical Research. Aug. 31, 2016;43(4):786.
Jacob et al., Solid State Crystallinity, Amorphous State, and Its Implications in the Pharmaceutical Process. IJPSR. 2011;2(3):472-482.
Jiang et al., Research and Development of Sphingosine 1-Phosphate Modulators. Progress in Pharmaceutical Sciences. Jul. 31, 2016;40(7):548-554.
Scott et al., Ozanimod (RPC1063) is a potent sphingosine-1-phosphate receptor-1 (S1P1 ) and receptor-5 (S1P5 ) agonist with autoimmune disease-modifying activity. Br J Pharmacol. 2016;173(11):1778-1792.
International Search Report and Written Opinion for Application No. PCT/CN2017/088314, dated Aug. 30, 2017, 13 pages.

*Primary Examiner* — Shawquia Jackson
(74) *Attorney, Agent, or Firm* — McCarter & English, LLP; Wei Song

(57) ABSTRACT

The present disclosure is related to crystalline forms of ozanimod hydrochloride, as well as preparation method thereof. The crystalline form of ozanimod hydrochloride provided by the present disclosure can be used for treating autoimmune diseases, particularly multiple sclerosis and ulcerative colitis. The crystalline form of the present disclosure has advantages in at least one aspect of solubility, melting point, stability, dissolution, bioavailability and processability and provides a new and better choice for the preparation of drug product containing ozanimod, and has significant value for drug development.

9 Claims, 6 Drawing Sheets (I)

CRYSTALLINE FORM OF OZANIMOD HYDROCHLORIDE, AND PROCESSES FOR PREPARATION THEREOF

CROSS-REFERENCE TO RELATED APPLICATIONS

This application is a U.S. national stage filing, under 35 U.S.C. § 371(c), of International Application No. PCT/CN2018/102034, filed on Aug. 23, 2018, which claims priority to Chinese Patent Application No. 201710768645.3, filed on Aug. 31, 2017. The entire contents of each of the aforementioned applications are incorporated herein by reference.

TECHNICAL FIELD

The present disclosure relates to the field of pharmaceutical chemistry, specifically relates to crystalline form of ozanimod hydrochloride, and processes for preparation thereof.

BACKGROUND

Multiple sclerosis (MS) is a central nervous system demyelinating disease, which is common in young and middle age. The clinical features are the widespread lesions and the commonly see symptoms are relapsing-remitting nervous system damage. The pathogenesis of multiple sclerosis is still unclear. Globally, multiple sclerosis affects about 2.3 million people. Most of them are RFMS (Relapsing forms of MS, RFMS), up to about 85%. PRMS (Progressive relapsing MS, PRMA) and PPMS (Primary progressive MS, PPMS) comprise 5% and 10%, respectively. Despite the low global morbidity multiple sclerosis has always been one of the most vivacious areas of pharmaceutical markets. More than five new drugs have been approved from 2010. From 2011 to 2016, annual composite growth rate of MS market is 12%. Globally, the MS drug market is expected to increase to $23 billion in 2022.

Ozanimod is a novel, oral, selective modulator of sphingosine-1-phosphate 1 receptor (S1P1R) developed by Receptos for the treatment of autoimmune diseases. In clinical trials, ozanimod has very good pharmacokinetic, pharmacodynamic and safety data, which can meet the development strategy and is expected to be the best second-generation SIP1R modulator drug. The chemical structure of ozanimod is shown as formula (I) and it is an S-enantiomer (hereinafter referred to as "Compound (I)")

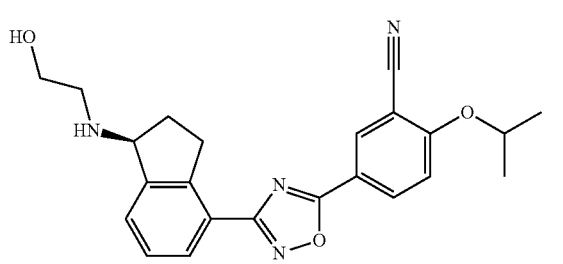

formula (I)

CN1102762100B is related to Compound (I) hydrochloride, and it only discloses the preparation method of the R-enantiomer of ozanimod, and not discloses preparation method, solid form or crystalline form of the ozanimod.

Therefore, it is necessary to perform comprehensive polymorph screening of ozanimod to realize its pharmacological development and release its potential, which will further facilitate the preparation of better drug products containing ozanimod.

The inventors of the present disclosure tried different methods and surprisingly discovered crystalline form CS2 of Compound (I) hydrochloride, which has advantages in at least one aspect of stability, melting point, solubility, in vitro and in vivo dissolution, hygroscopicity, bioavailability, adhesiveness, compressibility, flowability, processability, purification ability, and formulation production, etc. Particularly. crystalline form CS2 of Compound (I) hydrochloride has good stability, high solubility, good dissolution and uniform particle size, which provides a new and better choice for the development of drug product containing ozanimod and is of great significance.

SUMMARY

The main objective of the present disclosure is to provide novel crystalline forms of Compound (I) hydrochloride, processes for preparation and use thereof.

According to the objective of the present disclosure, crystalline form CS2 of Compound (I) hydrochloride is provided (hereinafter referred to as Form CS2).

According to one aspect of the present disclosure, the X-ray powder diffraction pattern of Form CS2 shows characteristic peaks at 2theta values of $19.7°\pm0.2°$, $7.8°\pm0.2°$, $14.4°\pm0.2°$ and $18.8°\pm0.2°$ using Cu-Kα radiation.

Furthermore, the X-ray powder diffraction pattern of Form CS2 shows one or more characteristic peaks at 2theta values of $4.0°\pm0.2°$, $15.1°\pm0.2°$ and $20.6°\pm0.2°$. Preferably, the X-ray powder diffraction pattern of Form CS2 shows characteristic peaks at 2theta values of $4.0°\pm0.2°$, $15.1°\pm0.2°$ and $20.6°\pm0.2°$.

Furthermore, the X-ray powder diffraction pattern of Form CS2 shows one or two characteristic peaks at 2theta values of $13.9°\pm0.2°$ and $12.7°\pm0.2°$. Preferably, the X-ray powder diffraction pattern of Form CS2 shows characteristic peaks at 2theta values of $13.9°\pm0.2°$ and $12.7°\pm0.2°$.

Furthermore, the X-ray powder diffraction pattern of Form CS2 shows one or more characteristic peaks at 2theta values of $13.0°\pm0.2°$, $13.3°\pm0.2°$ and $11.8°\pm0.2°$. Preferably, the X-ray powder diffraction pattern of Form CS2 shows characteristic peaks at 2theta values of $13.0°\pm0.2°$, $13.3°\pm0.2°$ and $11.8°\pm0.2°$.

According to another aspect of the present disclosure, the X-ray powder diffraction pattern of Form CS2 shows three or four or five or six or seven or eight or nine or ten or eleven or twelve characteristic peaks at 2theta values of $19.7°\pm0.2°$, $7.8°\pm0.2°$, $14.4°\pm0.2°$, $18.8°\pm0.2°$, $15.1°\pm0.2°$, $20.6°\pm0.2°$, $13.9°\pm0.2°$, $12.7°\pm0.2°$, $13.0°\pm0.2°$, $13.3°\pm0.2°$ and $11.8°\pm0.2°$ using Cu-Kα radiation.

Without any limitation being implied, the X-ray powder diffraction pattern of Form CS2 is depicted in FIG. 1.

According to the objective of the present disclosure, a process for preparing Form CS2 is also provided. The process comprises: dissolving Compound (I) hydrochloride into a solvent mixture of ethers and water, then evaporating slowly to obtain Form CS2.

Furthermore, said ether is tetrahydrofuran; furthermore, said volume ratio of tetrahydrofuran and water is 19:1.

According to the objective of the present disclosure, a pharmaceutical composition is provided, said pharmaceutical composition comprises a therapeutically effective amount of Form CS2 and pharmaceutically acceptable carriers, diluents or excipients.

Furthermore, Form CS2 provided by present disclosure can be used for preparing drugs of selective modulator of sphingosine-1-phosphate receptor.

Furthermore, Form CS2 provided by present disclosure can be used for preparing drugs for treating ulcerative colitis.

Furthermore, Form CS2 provided by present disclosure can be used for preparing drugs for treating multiple sclerosis.

Form CS2 of the present disclosure has the following advantages:

(1) Form CS2 of the present disclosure has good physicochemical stability. Form CS2 doesn't change for at least 7 weeks when stored under the conditions of 25° C./60% RH, 40° C./75% RH and 60° C./75% RH The chemical purity is above 99% and remains substantially unchanged when stored under the conditions of 25° C./60% RH and 40° C./75% RH for at least 7 weeks. Meanwhile, Form CS2 has good physical stability after grinding. Grinding and pulverization are often required in the formulation process. Good physical stability of the drug substance under grinding condition can reduce the risk of crystallinity decrease and crystal transformation during the formulation process.

Crystal transformation can lead to changes in the absorption of the drug and even cause toxicity and side effects. Especially, the concentration change at the target organ can directly affect the toxicity and side effects of the drug. Form CS2 has good physical and chemical stability, which can ensure the consistent and controllable quality of the drug substance and drug product, minimize the toxicity due to crystal transformation, and guarantee the efficacy of the drug.

(2) Form CS2 of the present disclosure has higher solubility. Higher solubility is beneficial to improve drug's in vivo absorption and bioavailability, thus improving drug efficacy. In addition, drug dose reduction without affecting efficacy is possible due to higher solubility, thereby reducing the drug's side effects and improving drug safety.

(3) Form CS2 of the present disclosure has lower hygroscopicity. The test results show that the weight gain of Form CS2 at 80% RH is 2.34%.

Hygroscopicity affects the stability of the drug, flowability and uniformity during production process, thereby affecting the quality of the drug product. Moreover, hygroscopicity affects the production, post-process and storage of drug. The crystalline form with low hygroscopicity is not demanding on the environment, which reduces the cost of production, storage and quality control, and has strong economic value.

(4) The capsule of Form CS2 of the present disclosure has good dissolution and dissolution rate. Form CS2 of the present disclosure is prepared into capsule. The dissolution profile is tested in pH 6.8 phosphate buffer solution containing 0.5% lauryl sodium sulfate. The result shows that the dissolution of the capsule of Form CS2 at 30 minutes is up to more than 85%, which indicates that the capsule using Form CS2 of the present disclosure as active ingredient has good dissolution and dissolution rate.

Drugs with different crystalline forms may lead to different in vivo dissolution rates, which directly affects the in vivo absorption, distribution, excretion and metabolism, and finally leads to difference in clinical efficacy due to different bioavailability. Dissolution and dissolution rates are important prerequisites for drug absorption. Good in vitro dissolution leads to higher in vivo absorption, better in vivo exposure, thereby improving drug's bioavailability and efficacy. High dissolution rate is beneficial for the drug to achieve peak concentration in plasma quickly after administration, thus ensuring rapid drug action.

Furthermore, Form CS2 of the present disclosure also has the following advantages:

Form CS2 of the present disclosure has uniform particle size distribution. The uniform particle size helps to simplify the post-process of the drug preparation process, such as reduce the grinding, which can reduce the cost. Also, the risk of crystallinity decrease and crystal transformation caused by grinding can be reduced, which will improve the quality control of drug products.

In the process of preparing Form CS2 of present disclosure:

Said "evaporating" is accomplished by using a conventional method in the field such as slow evaporation or rapid evaporation. Slow evaporation is accomplished in a container covered by sealing film with pinholes. Rapid evaporation is accomplished in an open container.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of +0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein and the "XRPD pattern is same" as described herein is not meaning absolutely the same, the same peak position can differ by ±0.2° and the peak intensity allows for some variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, crystalline Form CS2 of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the numerical value and the scope of the present disclosure should not be narrowly understood as a value or numerical value range. It should be understood by those skilled in the art that the specific numerical value can be floated according to the specific technical environment on the basis that the spirit and principle of the disclosure are not depart from the spirit and principle of the disclosure. In the present disclosure, the number of floating ranges which can be expected by one of skilled in the art is represented by the term"about".

DETAILED DESCRIPTION OF THE DISCLOSURE

Figure 1:
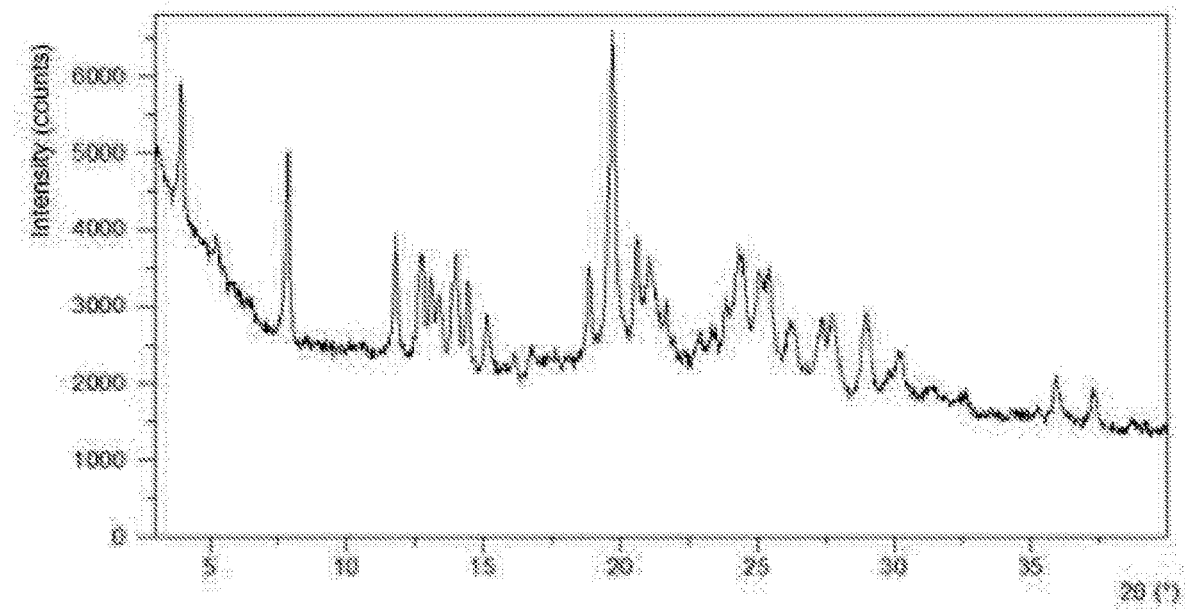
FIG. 1 shows an XRPD pattern of Form CS2 in example 1.

The present disclosure is further illustrated by the following examples in detail, but is not intended to limit the scope of the present disclosure. The skilled in the art can make improvements to the process of preparation and the instruments used within the scope of the claims, and those improvements should be considered as falling into the scope of the present disclosure. Therefore, the protective scope of the present disclosure patent should be defined by the claims.

In the following examples, the test method is generally implemented according to a conventional condition or a condition recommended by manufacturer.

The abbreviations used in the disclosure are explained as follows:
XRPD: X-ray Powder Diffraction
DSC: Differential Scanning calorimetry
TGA: Thermal Gravimetric Analysis
DVS: Dynamic Vapor Sorption
PSD: Particle Size Distribution
$^1$H NMR: Proton Nuclear Magnetic Resonance X-ray powder diffraction pattern in the present disclosure was acquired by a Panalytical Empyrean X-ray powder diffractometer. The parameters of the X-ray powder diffraction method of the present disclosure were as follows:
X-ray Reflection: Cu, Kα.
Kα1 (Å): 1.540598; Kα2 (ÅA): 1.544426
Kα2/Kα1 intensity ratio: 0.50
Voltage: 45 (kV)
Current: 40 (mA)
Scan range: from 3.0 to 40.0 degree Differential scanning calorimetry (DSC) data in the present disclosure were acquired by a TA Q2000. The parameters of the differential scanning calorimetry (DSC) method of the present disclosure were as follow:
Heating rate: 10° C./min
Purge gas: nitrogen Thermal gravimetric analysis (TGA) data in the present disclosure were acquired by a TA Q500. The parameters of the thermal gravimetric analysis (TGA) method of the present disclosure were as follows:
Heating rate: 10° C./min
Purge gas: nitrogen Dynamic Vapor Sorption (DVS) is measured via a SMS (Surface Measurement Systems Ltd.) intrinsic DVS instrument. Its control software is DVS-Intrinsic control software, and its analysis software is DVS-Intrinsic Analysis software. Typical Parameters for DVS test are as follows:
Temperature: 25° C.
Gas and flow rate: N$_2$, 200 mL/min
dm/dt: 0.002%/min
RH range: 0% RH to 95% RH High Performance Liquid Chromatography (HPLC) data for purity test in example 4 of the present disclosure were collected from an Agilent 1260 with UV Variable Wavelength Detector (VWD). The HPLC method parameters are as follows:
Column: Waters XBridge C18 150×4.6 mm, 5 μm
Mobile Phase: A: 0.1% TFA in H$_2$O
B: 0.1% TFA in Acetonitrile
Gradient:

| Time (min) | % B |
|---|---|
| 0.0 | 10 |
| 12.0 | 40 |
| 20.0 | 90 |
| 25.0 | 90 |
| 25.1 | 10 |
| 30.0 | 10 |

Flow rate: 1.0 mL/min
Injection Volume: 10 μL
Detection wavelength: 270 nm
Column Temperature: 40° C.
Diluent: MeOH/THF (v/v, 6/4)

High Performance Liquid Chromatography (HPLC) data for solubility test in example 5 of the present disclosure were collected from an Agilent 1100 with Diode Array Detector (DAD). The HPLC method parameters are as follows:
Column: L005# Waters Xbridge C18, 150×4.6 mm, 5 μm
Mobile Phase: A: 0.1% TFA in H$_2$O
B: 0.1% TFA in Acetonitrile
Gradient:

| Time (min) | % B |
|---|---|
| 0.0 | 25 |
| 10.0 | 50 |
| 12.0 | 80 |
| 15.0 | 80 |
| 15.1 | 25 |
| 20.0 | 25 |

Flow rate: 1.0 ml/min
Injection Volume: 5 μl

Detection wavelength: 270 nm
Column Temperature: 40° C.
Diluent: MeOH/THF (v/v, 6/4)

High Performance Liquid Chromatography (HPLC) data for dissolution test in example 8 of the present disclosure were collected from an Agilent 1100 with UV Variable Wavelength Detector (VWD). The HPLC method parameters are as follows:

Column: 75 Waters Xbridge C18, 150×4.6 mm, 5 μm
Mobile Phase: A: 0.1% TFA in $H_2O$
B: 0.1% TFA in Acetonitrile
Gradient:

| Time (min) | % B |
|---|---|
| 0 | 25 |
| 10.0 | 50 |
| 12.0 | 80 |
| 15.0 | 80 |
| 15.1 | 25 |
| 20.0 | 25 |

Flow rate: 1.0 mL/min
Injection Volume: 10 μL
Detection wavelength: 270 nm
Column Temperature: 40° C.
Diluent: MeOH/THF (v/v, 6/4)

The particle size distribution data in the present disclosure were acquired by an S3500 laser particle size analyzer of Microtrac. Microtrac S3500 is equipped with an SDC (Sample Delivery Controller). The test is carried out in wet mode, and the dispersion medium is Isopar G. The parameters are as follows:

| | |
|---|---|
| Size distribution: Volume | Run Time: 10 s |
| Dispersion medium: Isopar G | Particle coordinates: Standard |
| Run Number: Average of 3 runs | Fluid refractive index: 1.42 |
| Particle Transparency: Trans | Residuals: Enabled |
| Particle refractive index: 1.5 | Flow rate: 60%* |
| Particle shape: Irregular | Filtration: Enabled |
| Ultrasonication power: 30 W | Ultrasonication time: 60 s |

*Flow rate 60% is 60% of 65 mL/s.

Proton nuclear magnetic resonance spectrum data ($^1H$ NMR) were collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL.

Unless otherwise specified, the following examples were conducted at room temperature. Said "room temperature" is not an exact temperature value but refers to 10-30° C.

According to the present disclosure, ozanimod hydrochloride as a raw material includes solid form (crystalline or amorphous), semisolid form, wax form or oil form. Preferably, compound (I) hydrochloride as a raw material is a solid.

Raw materials of ozanimod hydrochloride used in the following examples are prepared by methods disclosed in CN102762100B.

Example 1

Preparation of Form CS2

About 20.4 mg of ozanimod hydrochloride was added into a 20-mL grass vial followed by adding 5 mL of solvent mixture of tetrahydrofuran and water (19:1, v/v). The solution was filtered and about 0.2 mg of polymer (said polymer is a mixture of polycaprolactone, polyoxyethylene, polymethyl methacrylate, sodium alginate, and hydroxyethyl cellulose and the mass ratio is 1:1:1:1:1) was added into the clear solution. And then the solution was stored at room temperature for slow evaporation until white solid obtained.

The obtained solid in this example was confirmed to be Form CS2. The X-ray powder diffraction data of the obtained solid are shown in Table 1, while the XRPD pattern is depicted in FIG. 1.

TABLE 1

| 2θ | d spacing | Intensity % |
|---|---|---|
| 3.95 | 22.34 | 77.36 |
| 5.21 | 16.97 | 33.12 |
| 7.83 | 11.29 | 57.15 |
| 11.77 | 7.52 | 34.29 |
| 12.73 | 6.95 | 30.23 |
| 13.07 | 6.78 | 24.22 |
| 13.35 | 6.63 | 18.90 |
| 13.99 | 6.33 | 32.14 |
| 14.41 | 6.15 | 24.96 |
| 15.09 | 5.87 | 16.19 |
| 16.11 | 5.50 | 4.67 |
| 16.71 | 5.30 | 5.94 |
| 18.85 | 4.71 | 32.67 |
| 19.71 | 4.51 | 100.00 |
| 20.58 | 4.32 | 42.16 |
| 21.04 | 4.22 | 36.00 |
| 21.64 | 4.11 | 24.52 |
| 22.86 | 3.89 | 15.48 |
| 23.37 | 3.81 | 16.20 |
| 23.80 | 3.74 | 23.96 |
| 24.31 | 3.66 | 41.05 |
| 25.04 | 3.56 | 35.78 |
| 25.43 | 3.50 | 34.33 |
| 26.32 | 3.39 | 20.48 |
| 27.33 | 3.26 | 22.88 |
| 27.70 | 3.22 | 25.68 |
| 28.93 | 3.09 | 27.52 |
| 30.19 | 2.96 | 15.49 |
| 31.32 | 2.86 | 6.18 |
| 37.51 | 2.75 | 4.94 |
| 35.88 | 2.50 | 12.98 |
| 37.21 | 2.42 | 8.54 |

Figure 2:
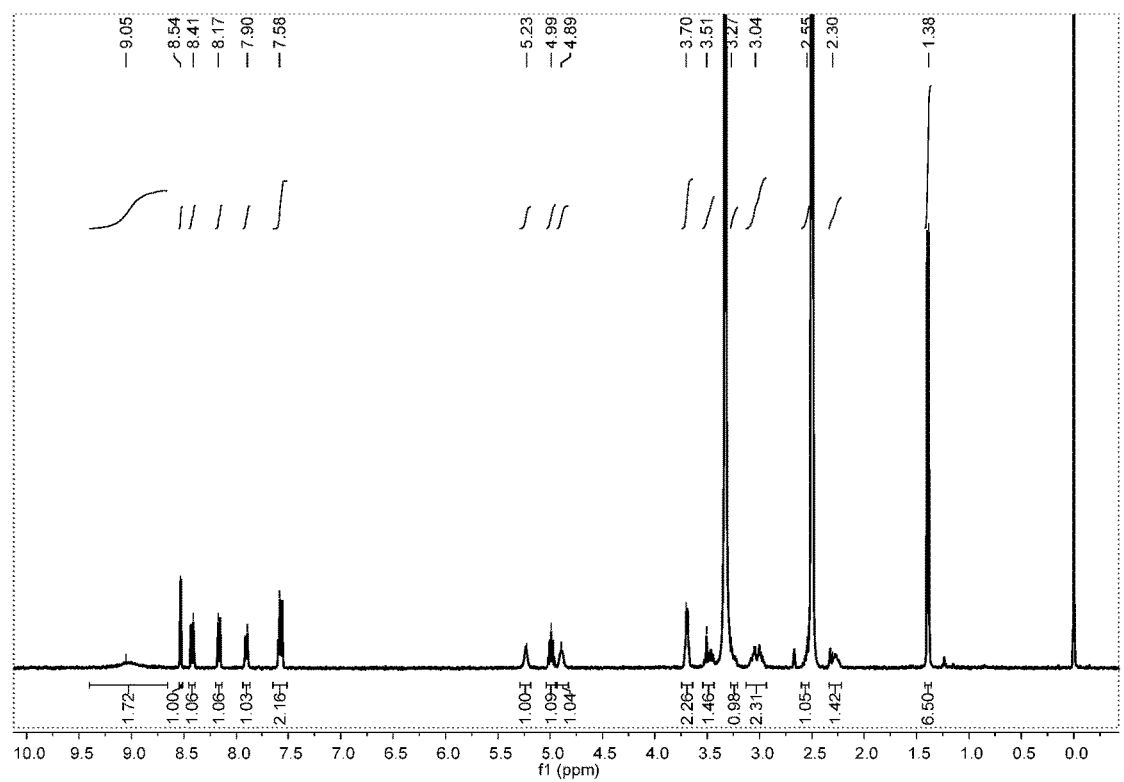
FIG. 2 shows a $^1$H NMR spectrum of Form CS2 in example 1.

The $^1H$ NMR spectrum of Form CS2 is depicted in FIG. 2, and the corresponding data are: $^1H$ NMR (400 MHz, DMSO) δ 9.06 (s, 2H), 8.56-8.51 (d, 1H), 8.42 (dd, 1H), 8.16 (d, 1H), 7.90 (d, 1H), 7.58 (m, 2H), 5.23 (s, 1H), 4.99 (m, 1H), 4.89 (s, 1H), 3.69 (q, 2H), 3.59-3.42 (m, 1H), 3.27 (m, 1H), 3.02 (ddd, 2H), 2.51 (m, 1H), 2.31-2.17 (m, 1H), 1.39 (d, 6H).

Example 2

Preparation of Form CS2

About 5.4 mg of ozanimod hydrochloride was added into a 5-mL grass vial followed by adding 5 mL of solvent mixture of tetrahydrofuran and water (19:1, v/v). The solution was filtered and then stored at room temperature for slow evaporation until white solid obtained.

Figure 3:
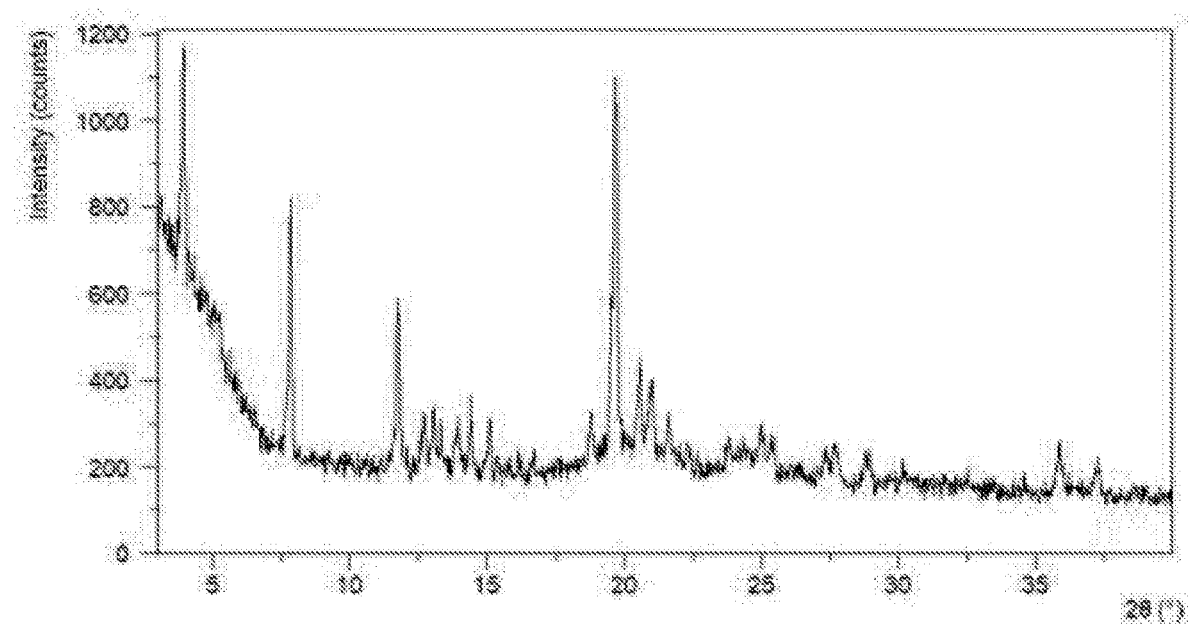
FIG. 3 shows an XRPD pattern of Form CS2 in example 2.

The obtained solid in this example was confirmed to be Form CS2. The X-ray powder diffraction data of the obtained solid are shown in Table 2, while the XRPD pattern is depicted in FIG. 3.

TABLE 2

| 2θ | d spacing | Intensity % |
|---|---|---|
| 3.89 | 22.72 | 100.00 |
| 5.12 | 17.27 | 38.84 |
| 7.79 | 11.34 | 60.88 |
| 8.96 | 9.87 | 6.40 |
| 11.11 | 7.97 | 5.05 |
| 11.73 | 7.55 | 41.68 |
| 12.09 | 7.32 | 5.53 |
| 12.67 | 6.99 | 15.28 |
| 13.02 | 6.80 | 17.75 |
| 13.28 | 6.67 | 15.43 |
| 13.86 | 6.39 | 10.79 |
| 14.37 | 6.17 | 18.37 |
| 15.07 | 5.88 | 16.56 |
| 16.10 | 5.51 | 5.85 |
| 16.66 | 5.32 | 7.38 |
| 18.78 | 4.73 | 17.03 |
| 19.65 | 4.52 | 90.59 |
| 20.54 | 4.32 | 25.95 |
| 20.99 | 4.23 | 24.32 |
| 21.60 | 4.11 | 14.84 |
| 22.28 | 3.99 | 9.94 |
| 23.74 | 3.75 | 8.79 |
| 24.98 | 3.57 | 12.45 |
| 25.35 | 3.51 | 9.61 |
| 26.31 | 3.39 | 4.41 |
| 27.31 | 3.27 | 8.23 |
| 27.66 | 3.22 | 7.99 |
| 28.98 | 3.08 | 4.61 |
| 30.16 | 2.96 | 4.39 |
| 35.84 | 2.51 | 11.40 |
| 37.24 | 2.41 | 7.50 |
| 38.11 | 2.36 | 1.95 |

Example 3

Preparation of Form CS2

About 100 mg of ozanimod hydrochloride was added into a 20-mL, grass vial followed by adding 20 mL of solvent mixture of tetrahydrofuran and water (19:1, v/v). The solution was filtered and then stored at room temperature for fast evaporation until white solid obtained.

Figure 4:
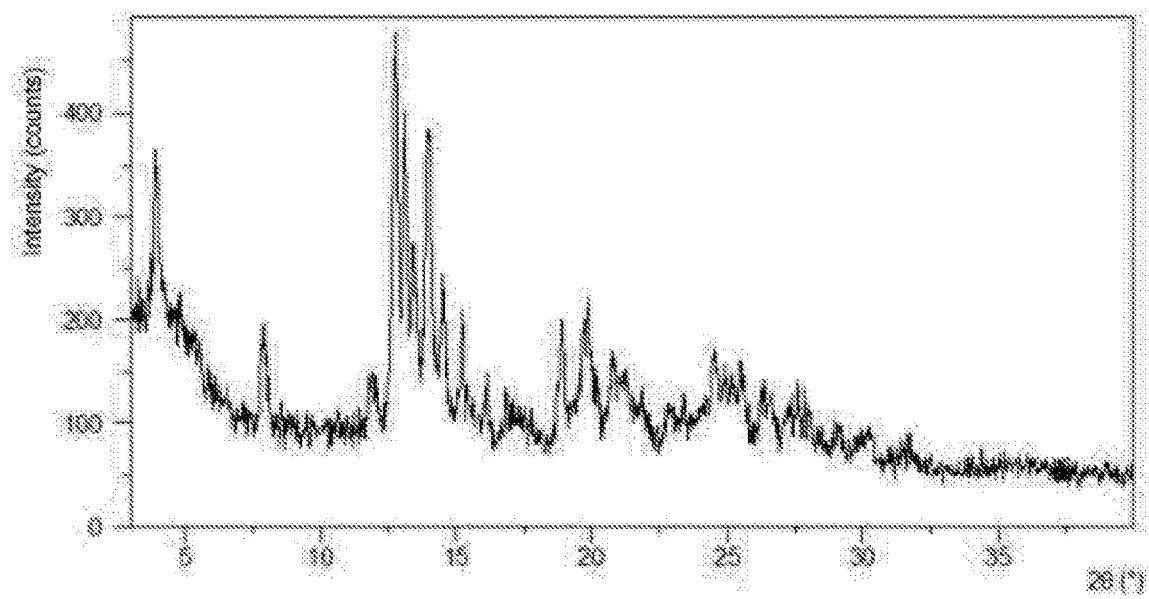
FIG. 4 shows an XRPD pattern of Form CS2 in example 3.

The obtained solid in this example was confirmed to be Form CS2. The X-ray powder diffraction data of the obtained solid are shown in Table 3, while the XRPD pattern is depicted in FIG. 4.

TABLE 3

| 2θ | d spacing | Intensity % |
|---|---|---|
| 3.86 | 22.92 | 68.77 |
| 5.16 | 17.12 | 23.70 |
| 7.84 | 11.28 | 26.29 |
| 11.81 | 7.49 | 14.71 |
| 12.60 | 7.02 | 86.80 |
| 12.71 | 6.96 | 100.00 |
| 13.05 | 6.79 | 84.19 |
| 13.36 | 6.63 | 46.09 |
| 13.89 | 6.38 | 79.63 |
| 14.45 | 6.13 | 41.47 |
| 15.15 | 5.85 | 30.63 |
| 16.07 | 5.51 | 18.34 |
| 17.02 | 5.21 | 6.64 |
| 18.86 | 4.71 | 32.28 |
| 19.77 | 4.49 | 34.74 |

TABLE 3-continued

| 2θ | d spacing | Intensity % |
|---|---|---|
| 20.74 | 4.28 | 23.09 |
| 22.83 | 3.90 | 11.02 |
| 24.46 | 3.64 | 26.52 |
| 25.46 | 3.50 | 20.34 |
| 26.26 | 3.39 | 14.89 |
| 27.51 | 3.24 | 17.98 |
| 27.78 | 3.21 | 18.66 |
| 29.03 | 3.08 | 8.29 |
| 30.18 | 2.96 | 8.48 |
| 31.57 | 2.83 | 4.00 |

Figure 5:
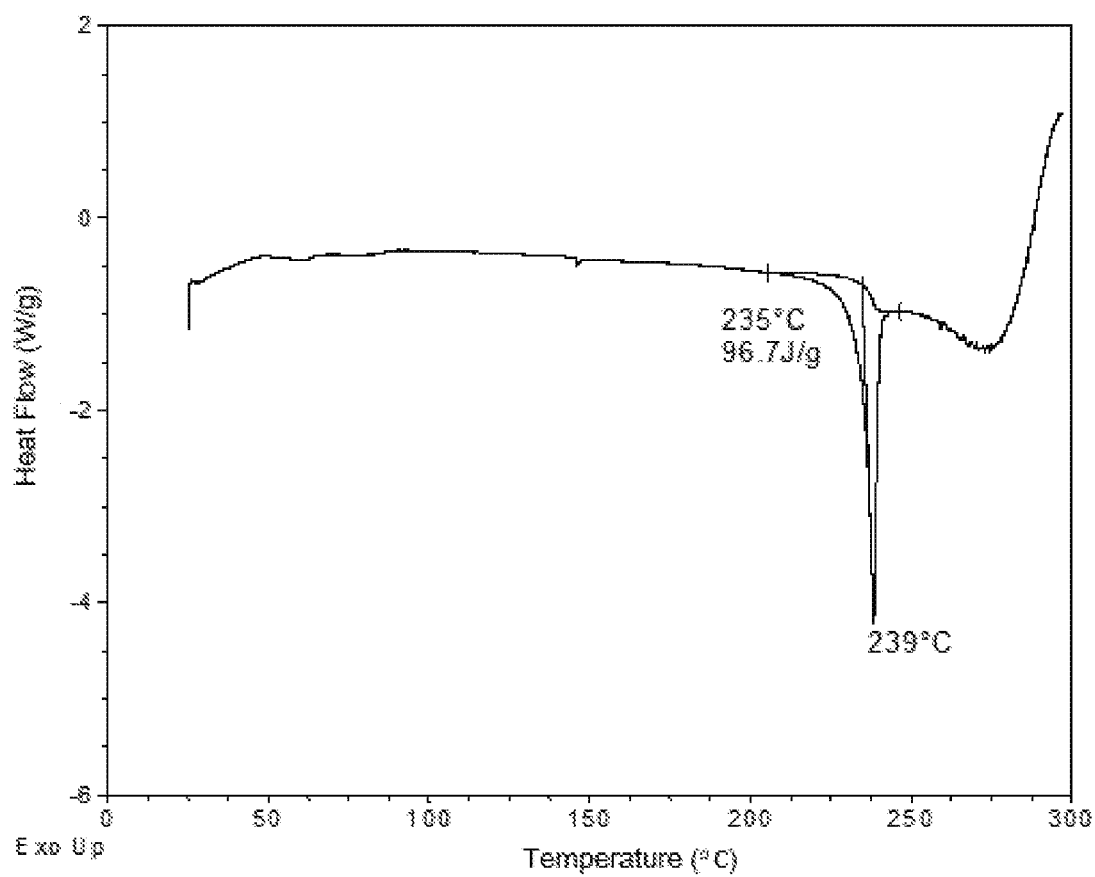
FIG. 5 shows a DSC curve of Form CS2 in example 3.

The DSC curve of Form CS2 is depicted in FIG. 5, which shows an endothermic peak with onset temperature at around 235° C.

Figure 6:
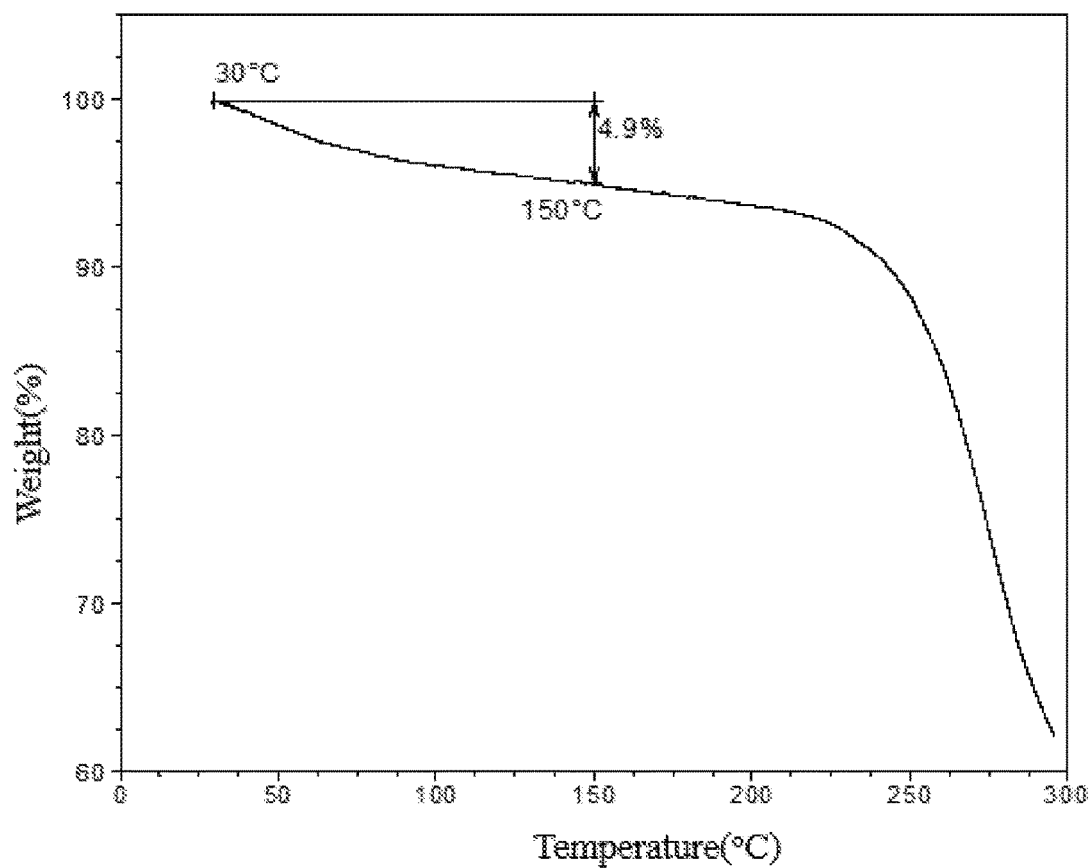
FIG. 6 shows a TGA curve of Form CS2 in example 3.

The TGA curve of Form CS2 is depicted in FIG. 6, which shows about 4.9% weight loss when heated to 150° C.

Example 4

Long-Term and Accelerated Stability of Form CS2

Figure 7:
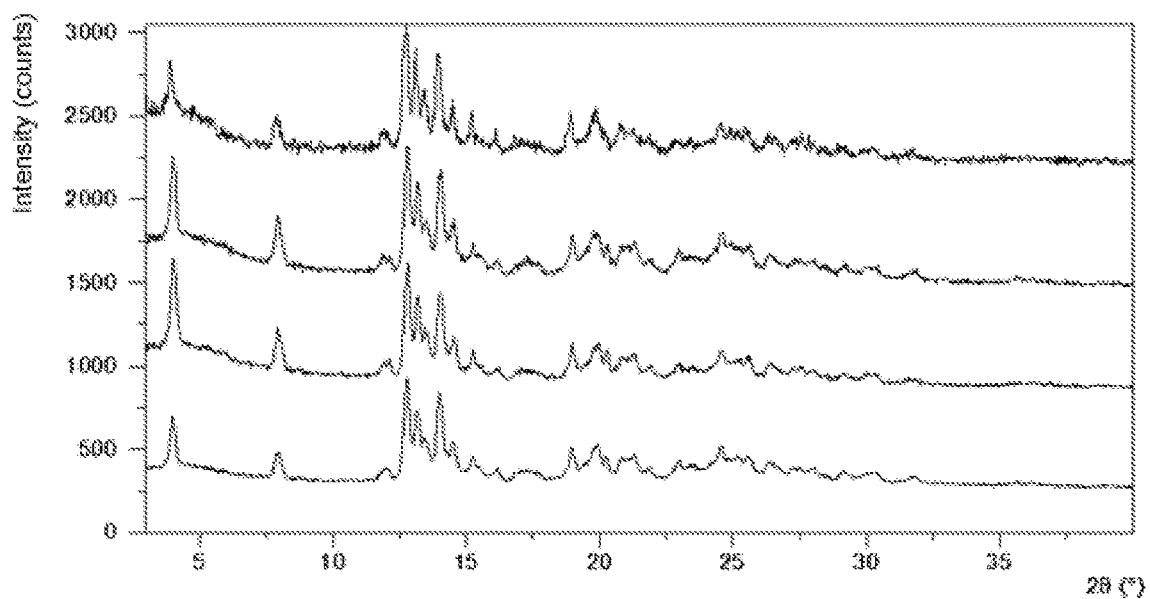
FIG. 7 shows an XRPD comparison pattern of Form CS2 before and after storage (from top to bottom: XRPD pattern of Form CS2 before and after being stored under conditions of 25° C./60% RH, 40° C./75% RH and 60° C./75% RH for 7 weeks)

Three solid samples of Form CS2 were stored under the conditions of 25° C./60% RH, 40° C./75% RH and 60° C./75% RH for 7 weeks in open dishes. XRPD of the samples was tested and the physical stability results are shown in FIG. 7 (from top to bottom: XRPD pattern of Form CS2 before and after being stored under the conditions of 25° C./60% RH, 40° C./75% RH and 60° C./75% RH for 7 weeks). Chemical purity of Form CS2 was tested after stored under the conditions of 25° C./60% RH and 40° C./75% RH for 7 weeks and the results are shown in Table 4.

TABLE 4

| Samples | Conditions | Purity after storage % |
|---|---|---|
| Sample 1 | 25° C./60%RH | 99.14% |
| Sample 2 | 40° C./75%RH | 99.07% |

The results show that there is no form change for Form CS2 after being stored at 25° C./60% RH, 40° C./75% RH and 60° C./75% RH for 7 weeks and the purity of Form CS2 is higher than 99% after being stored at 25° C./60% RH and 40° C./75% RH for 7 weeks. The results show that Form CS2 has good stability.

Example 5

Dynamic Solubility of Form CS2

Simulated gastrointestinal fluids such as SGF (Simulated gastric fluids), FaSSIF (Fasted state simulated intestinal fluids) and FeSSIF (Fed state simulated intestinal fluids) are biorelevant media. Solubility in such media is closer to that in human environment, which can reflect the effects of gastrointestinal environment on drug release better.

20 mg of Form CS2 was suspended into 1.5 mL of SGF, 1.5 mL of FaSSIF, 1.5 mL of FaSSIF and 1.5 mL of water to get saturated solutions. After equilibrated for 1 h, 4 h and 24 h, concentrations (mg/mL) of the saturated solutions were measured by HPLC. The results are listed in Table 5.

TABLE 5

| Time | Solubility mg/mL | | | |
|---|---|---|---|---|
| | SGF CS2 | FeSSIF CS2 | FaSSIF CS2 | H$_2$O CS2 |
| 1 h | 0.20 | 0.30 | 3.0 | 2.1 |
| 4 h | 0.21 | 0.28 | 3.0 | 2.2 |
| 24 h | 0.24 | 0.32 | 3.1 | 2.4 |

The results show that the solubility of Form CS2 is high in SGF, FaSSIF, FaSSIF and H$_2$O.

Example 6

Mechanical Stability of Form CS2

Figure 8:
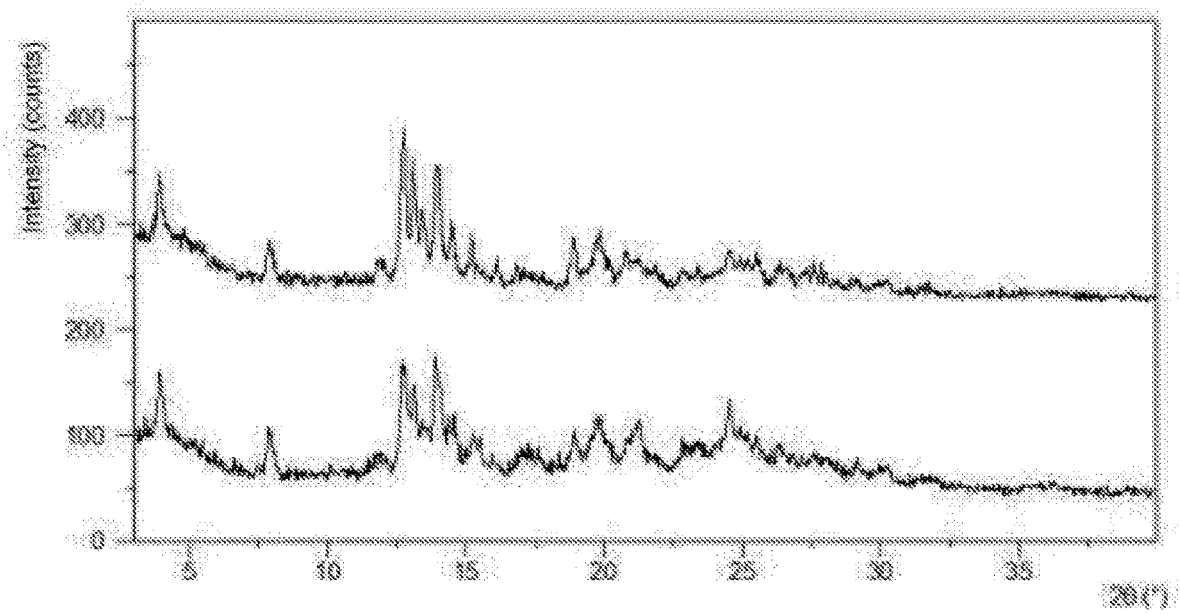
FIG. 8 shows an XRPD comparison pattern of Form CS2 before and after grinding (the top pattern is Form CS2 before grinding and the bottom pattern is Form CS2 after grinding)

Solid sample of Form CS2 was ground manually for 5 minutes in a mortar. The XRPD comparison pattern of Form CS2 before and after grinding is depicted in FIG. 8.

The results show that the crystalline form of Form CS2 doesn't change after grinding, which indicates that Form CS2 has good mechanical stability.

Example 7

Hygroscopicity of Form CS2

Figure 9:
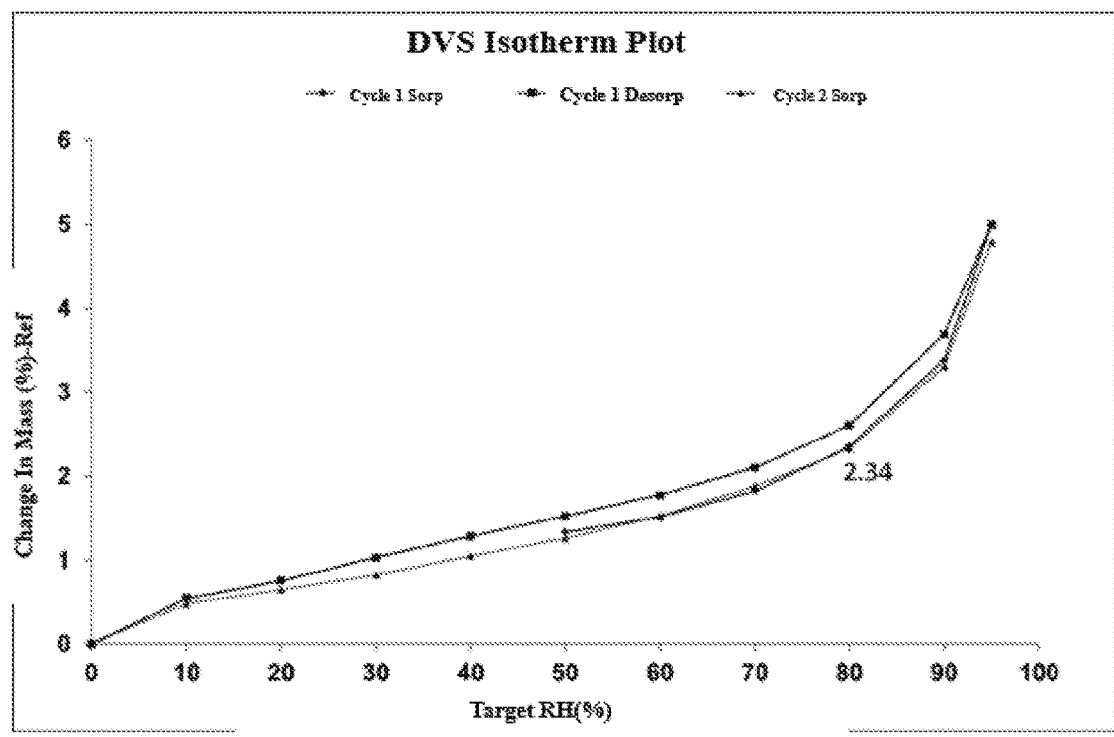
FIG. 9 shows a DVS plot of Form CS2.

Dynamic vapor sorption (DVS) was applied to test hygroscopicity of Form CS2 with about 10 mg of sample. The results were listed in Table 6. The DVS plot of Form CS2 is depicted in FIG. 9.

TABLE 6

| Form | Weight gain Weight gain under 80% RH |
|---|---|
| Form CS2 of ozanimod hydrochloride | 2.34% |

The results show that the weight gain of Form CS2 of ozanimod hydrochloride under 80% RH is 2.34% and the hygroscopicity is low.

Example 8

The Components and Dissolution of the Formulation of Form CS2

The components of the capsule of Form CS2 of ozanimod hydrochloride is shown in Table 7.

TABLE 7

| NO. | Component | mg/unit | % (w/w) | Function |
|---|---|---|---|---|
| | Intra-granular components | | | |
| 1 | Form CS2 of ozanimod hydrochloride | 1.10 | 1.60 | Active ingredient |
| 2 | Microcrystalline Cellulose (PH 101) | 58.58 | 93.90 | Filler |

TABLE 7-continued

| NO. | Component | mg/unit | % (w/w) | Function |
|---|---|---|---|---|
| 3 | Crospovidone (XL-10) | 1.25 | 2.00 | Disintegrator |
| 4 | Magnesium Stearate (5712) | 0.16 | 0.26 | Lubricant |
| | Extra-granular components | | | |
| 5 | Crospovidone (XL-10) | 1.25 | 2.00 | Disintegrator |
| 6 | Magnesium Stearate (5712) | 0.16 | 0.26 | Lubricant |
| Total | | 62.50 | 100.00 | — |

Note:
1.10 mg ozanimod hydrochloride is equivalent to 1.00 mg ozanimod freebase.

Preparation process is listed as following:
1. The intra-granular components were mixed uniformly;
2. The mixture materials were sieved by a 35 mesh sieve and then uniformly mixed again;
3. The mixture in step 2 is tableted by single punch manual tablet press (type: ENERPAC; die: φ y 20 mm round; tablet weight: 500 mg; pressure: 5±0.5 KN) and then the obtained tablet was crushed and sieved through a 20 mesh sieve;
4. The extra-granular components were uniformly mixed with the particles in step 3;
5. The final mixed powder was encapsulated into 4 # capsules. Content load: 62.5 mg;
6. The capsules were put into 35 cc HDPE bottles and sealed.

Dissolution test of the capsule of Form CS2 of ozanimod hydrochloride:

Paddle method (speed: 75 rpm) was used to test the dissolution in 900 mL pH 6.8 phosphate buffer solution containing 0.5% lauryl sodium sulfate. The samples were taken at 5 min, 10 min, 15 min, 20 min, 30 min, 45 min and 60 min.

Figure 10:
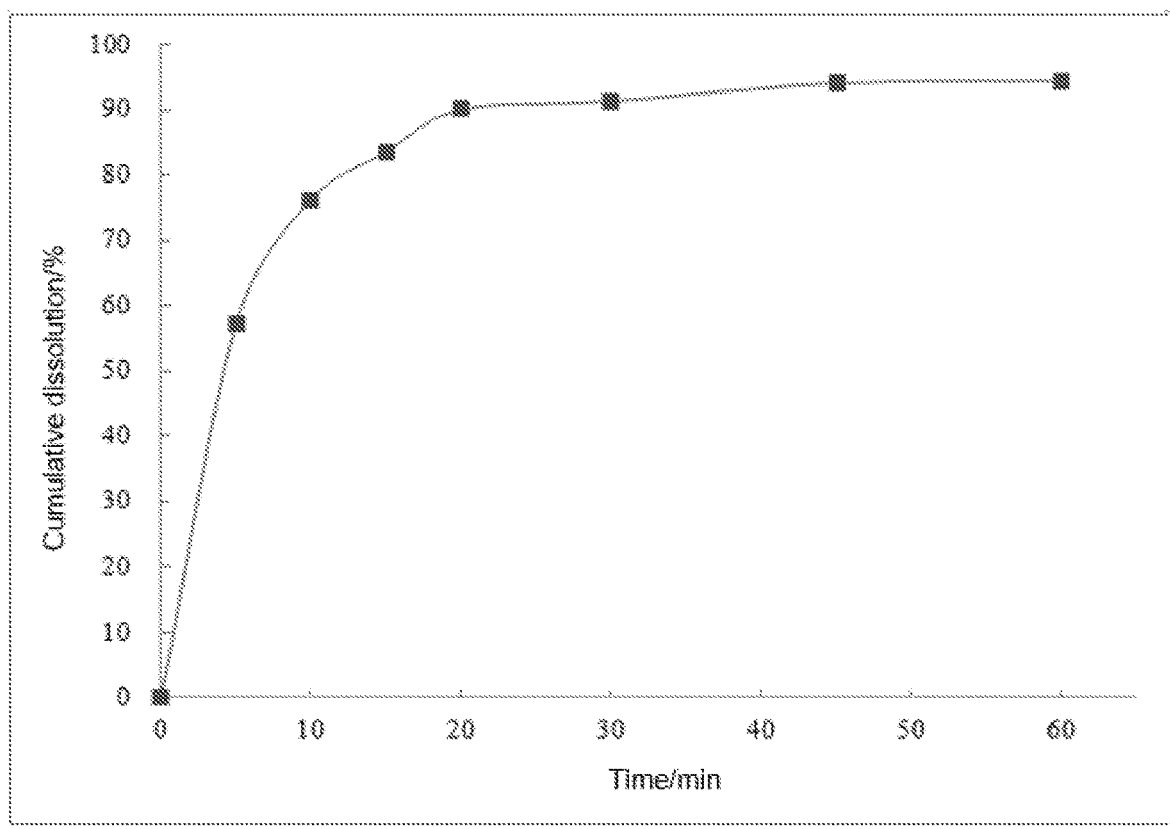
FIG. 10 shows a dissolution curve of Form CS2's capsule.

The test results are shown in table 8 and FIG. 10:

TABLE 8

| Time (min) | Accumulative drug release (%) |
|---|---|
| 0 | 0.00 |
| 5 | 57.32 |
| 10 | 76.17 |
| 15 | 83.47 |
| 20 | 90.02 |
| 30 | 91.28 |
| 45 | 94.14 |
| 60 | 94.51 |

As shown in Table 8 and FIG. 10, the dissolution of the Form CS2 capsule in pH 6.8 phosphate buffer solution comprising 0.5% lauryl sodium sulfate at 30 minutes is up to more than 85%, which indicates that the capsule using Form CS2 of the present disclosure as active ingredient has good dissolution and dissolution rate.

Example 9

Particle Size Distribution of Form CS2

Figure 11:
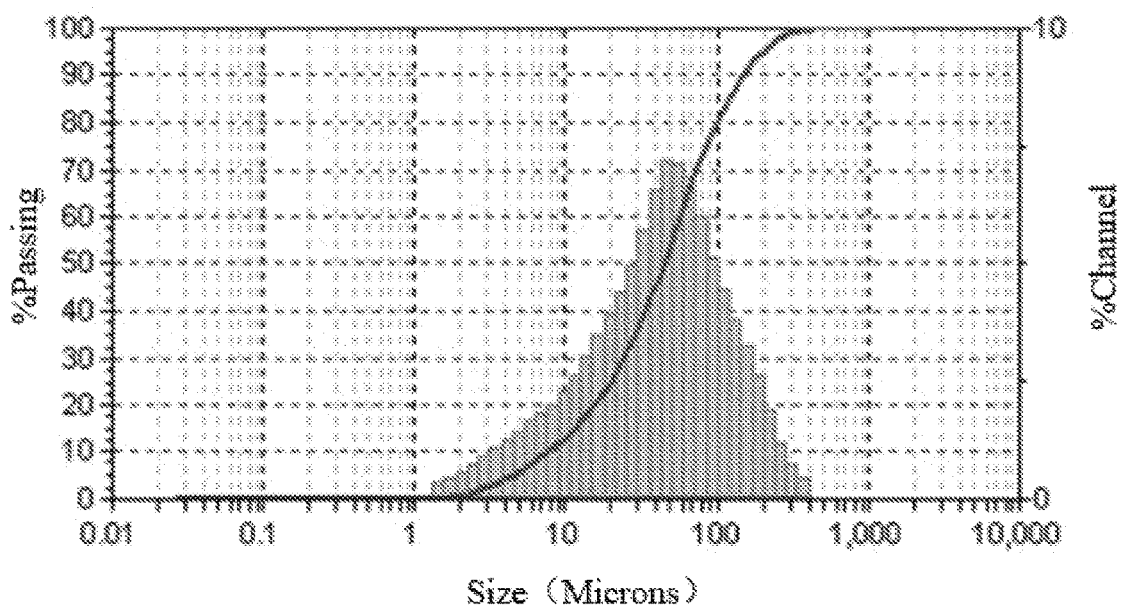
FIG. 11 shows a PSD diagram of Form CS2.

10-30 mg of Form CS2 and 10 mL of Isopar G (containing 0.2% lecithin) were mixed thoroughly and then transferred into the SDC. The measurement was started when the sample amount indicator is in appropriate position. The average particle diameter calculated by volume, the diameter at which 10% mass is comprised of smaller particles, the diameter at which 50% mass is comprised of smaller particles and the diameter at which 90% mass is comprised of smaller particles were obtained in particle size distribution test. The results are shown in Table 9. The particle size distribution diagram is shown in FIG. 11.

TABLE 9

| Form | MV (μm) | SD | D10 (μm) | D50 (μm) | D90 (μm) |
| --- | --- | --- | --- | --- | --- |
| CS2 | 64.22 | 51.36 | 7.6 | 44.90 | 149.4 |

Explanation of the abbreviations used in the present invention is as follows:

MV: Average particle diameter calculated by volume.

D10: the size in microns below which 10 percent of the particles reside on a volume basis.

D50: the size in microns below which 50 percent of the particles reside on a volume basis, also known as the median diameter.

D90: the size in microns below which 90 percent of the particles reside on a volume basis.

The results show that the average particle size of Form CS2 is about 64.22 μm, and the particle size distribution is almost normal distribution. The particle size distribution of Form CS2 is uniform.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:

1. A crystalline form CS2 of ozanimod hydrochloride, wherein the X-ray powder diffraction pattern shows characteristic peaks at 2theta values of 19.7°±0.2°, 7.8°±0.2°, 14.4°±0.2° and 18.8°±0.2° using Cu-Kα radiation.

2. The crystalline form CS2 of ozanimod hydrochloride according to claim 1, wherein the X-ray powder diffraction pattern shows one or two or three characteristic peaks at 2theta values of 4.0°±0.2°, 15.1°±0.2° and 20.6°±0.2° using Cu-Kα radiation.

3. The crystalline form CS2 of ozanimod hydrochloride according to claim 1, wherein the X-ray powder diffraction pattern shows one or two characteristic peaks at 2theta values of 13.9°±0.2° and 12.7°±0.2° using Cu-Kα radiation.

4. A process for preparing the crystalline form CS2 of ozanimod hydrochloride according to claim 1, wherein the process comprises: dissolving ozanimod hydrochloride into a solvent mixture of an ether and water, then evaporating slowly to obtain crystalline form CS2.

5. The process according to claim 4, wherein said ether is tetrahydrofuran, said volume ratio of tetrahydrofuran and water is 19:1.

6. A pharmaceutical composition, wherein said pharmaceutical composition comprises a therapeutically effective amount of the crystalline form CS2 of ozanimod hydrochloride according to claim 1 and a pharmaceutically acceptable carrier, a diluent or an excipient.

7. A method of activating sphingosine-1-phosphate receptor, comprising administering to a subject in need thereof a therapeutically effective amount of the crystalline form CS2 of ozanimod hydrochloride according to claim 1.

8. A method of treating ulcerative colitis, comprising administering to a subject in need thereof a therapeutically effective amount of the crystalline form CS2 of ozanimod hydrochloride according to claim 1.

9. A method of treating multiple sclerosis, comprising administering to a subject in need thereof a therapeutically effective amount of the crystalline form CS2 of ozanimod hydrochloride according to claim 1.

* * * * *